United States Patent [19]

Sexton

[11] 4,329,337

[45] May 11, 1982

[54] TURKEY SEMEN EXTENDER

[75] Inventor: Thomas J. Sexton, Bowie, Md.

[73] Assignee: The United States of America as represented by the Secretary of Agriculture, Washington, D.C.

[21] Appl. No.: 288,260

[22] Filed: Jul. 29, 1981

[51] Int. Cl.³ .............................................. A61K 35/48
[52] U.S. Cl. ........................................ 424/105; 435/2
[58] Field of Search ............................. 435/2; 424/105

[56] References Cited

U.S. PATENT DOCUMENTS 3,185,623  5/1965  Smith et al. ......................... 167/53.2
3,431,172  3/1969  Rajamannan ......................... 195/1.8
3,816,249  6/1974  Bhattacharya ......................... 195/1.8

OTHER PUBLICATIONS

Ostashko et al.–Chem. Abst., vol. 83 (1975), p. 209, 428d.
Sexton et al., Poultry Science 57, 277–284, 1978.
Sexton, Poultry Science 57, 285–289, 1978.

*Primary Examiner*—Sam Rosen
*Attorney, Agent, or Firm*—M. Howard Silverstein; William E. Scott; David G. McConnell

[57] ABSTRACT

A medium for preserving and extending the viable useful life of poultry semen, in vitro, is provided. Turkey semen is preserved without loss of fertility for up to 18 hours in the medium.

12 Claims, No Drawings

TURKEY SEMEN EXTENDER

BACKGROUND OF THE INVENTION

1. Field of the Invention

This invention relates to a medium for diluting and preserving poultry semen without critical loss in viability and more particularly to a medium for extending the useful life of poultry semen.

2. Description of the Art

A number of turkey semen diluents are commercially available and used by producers to extend semen (Calif. Agric., Aug. 15, 1970; Poultry Sci. 56, 1054-1056, 1977). A number of synthetic solutions that extend as well as aid in preservation of chicken semen have been formulated and tested (J. Reprod. Fert. 13, 571-575, 1967, J. Reprod. Fert. 57: 149-155, 1979; Poultry Sci. 56, 1443-1446, 1977). Researchers have concluded that chicken and turkey spermatozoa retain their full fertilizing ability in media having wide ranges in both osmolarity ($\Delta$, 0.455° to 0.736° C.) and pH level (6.0 to 8.0), Beltsville Symposium in Agricultural Research No. 3, Animal Reproduction, 1979, Chapter 12, pg. 161.

SUMMARY OF THE INVENTION

An object of this invention is to provide a medium for diluting and preserving poultry semen.

Another object is to provide a medium in which poultry spermatozoa can retain its fertility.

A further object is to provide a medium and method for extending the useful life of poultry semen, especially turkey semen.

A still further object is to provide an extender that will preserve turkey semen at 5° to 15° C. for from six to eighteen hours prior to using it for artificially inseminating female birds.

Still another object is to provide an extender that will permit collected turkey semen to be held for up to eighteen hours without any loss of fertility.

According to this invention the above objects are accomplished by a medium comprised of a mixture of salts, sugar and amino acids in amounts effective in aqueous solution to extend the viability of semen containing live spermatozoa and which is chemically balanced to provide the proper osmotic balance, hydrogen ion concentration, chelating action and energy required to extend the viability of the semen.

DETAILED DESCRIPTION OF THE INVENTION

Most turkeys throughout the world are bred by artificial insemination, not because of the genetic merit to be gained through artificial insemination but primarily because the size of the turkey male attained through genetic selection makes them unable to perform natural mating. Much effort is made to use a suitable diluent for extending semen in order to reduce production costs. Methods to store semen for at least six to eight hours would help to attain this objective. Consequently, intensive investigations have been made to determine what components and conditions are required for extending and preserving both chicken and turkey semen.

A number of synthetic solutions that extend as well as aid in semen preservation have been formulated and tested. Formulations have often been based on the composition and properties of seminal fluid. It has been determined that components selected for semen extenders should provide exogenous energy sources, proper osmotic balance, sufficient buffering capacity, control of bacterial growth, and some chelating action to protect against toxic ions. Some of the more common components used in poultry semen extenders are listed in Table 1.

Although it is not known which components in semen extenders are critical for the support of sperm viability during storage in vitro, it has been concluded by researchers in the field that chicken and turkey spermatozoa retain their full fertilizing ability in media having wide ranges in both osmolarity ($\Delta$, 0.455° to 0.736° C.) and pH level (pH 6.0 to 8.0). The optimal temperature for storing undiluted turkey semen appears to be 15° C.; even at this temperature, however, preservation without serious loss of fertilizing capacity has usually been limited to a few hours. Undiluted turkey semen is extraordinarily sensitive to temperatures above and below 15° C. Turkey spermatozoa usually perishes within a few minutes outside of the body even in its own seminal fluid. In fact, prior to this invention, diluted turkey semen lost considerable fertilizing capacity when stored in various diluents for six hours regardless of the temperature at which it was held. This is in contrast with the fertilizing capacity of diluted chicken semen which can be maintained for 24 to 48 hours without serious loss of that capacity when stored at 2° to 5° C.

In the United States alone, 3.5 million turkey hens are artificially inseminated each year at a cost of twelve million dollars. This invention provides a means of substantially reducing the cost of artificial insemination. Diluting semen 1:1 with the medium of this invention will reduce the number of breeder toms needed by 50%, which would save the industry about six million dollars. In addition, the labor requirement for artificial insemination could be reduced by 30% and save about an additional two to three million dollars.

In the practice of this invention semen containing live spermatozoa is collected birds either directly into the medium of this invention or into a tube and added to the medium and the mixture of semen and medium is stored at from 5° to 15° C. in vitro until it is used to inseminate a plurality of female birds. The medium of this invention, BPSE-II, has the following formulation:

| Constituent | Grams |
| --- | --- |
| Potassium diphosphate . 3H$_2$O | 12.70 |
| Sodium glutamate | 8.67 |
| Fructose (anhydrous) | 5.00 |
| Sodium acetate . 3H$_2$O | 4.30 |
| TES* | 1.95 |
| Potassium citrate | 0.64 |
| Potassium monophosphate | 0.65 |
| Magnesium chloride . 6H$_2$O | 0.34 |

*N-tris Hydroxymethyl methyl-2-Aminoethane Sulfonic Acid.

In preparing the medium, sterilized glassware or other type of container is used and filtering is done in a closed system. The prepared medium is dispensed in airtight containers. The weighed amount of each constituent is put into a large beaker or other container and the aggragate of constituents is mixed for about 30 to 60 minutes with 900 ml of distilled water. The pH of the medium is adjusted to 6.50±0.1 by addition of 12 N HCl and the osmolarity is adjusted to 350±10 m.osmols by addition of distilled water. The mixture is then filtered through a microfilter having a pore size of 0.22 millimicrons. Before packaging the medium in sterile vials or other suitable containers, it is tested by the brain-heart infusion medium technique to make certain that it does not contain any microbial contamination. The pH and osmolarity are also checked at this time.

BPSE-II is similar in composition to the extender found useful in extending the fertility of chicken semen, BSPE-I, (Poultry Science 56, 1443-1446, 1977). In fact, the only difference between BPSE-I and BPSE-II is in the pH and osmolarity of the mediums. However, although BSPE-I worked well with chicken semen under the conditions described, turkey semen lost considerable fertilizing capacity when stored in BPSE-I for six hours. In addition, with BPSE-II, I found that high levels of fertility (93%) could be maintained throughout the turkey hen reproduction cycle of 24 weeks. With BPSE-I, the level of fertility started to decline in the 10th week. Therefore, BPSE-II provides a significant improvement in performance over that of BPSE-I.

The greatly improved performance of BPSE-II over that of BPSE-I is shown in Table 2 where the effect of BPSE-I and BPSE-II on the fertility of turkey semen is compared over 15 weeks of an egg production cycle. Semen was collected from a plurality of male turkeys, half of which was mixed at a 1:1 ratio with BPSE-I and the other half at a 1:1 ratio with BPSE-II, each medium being at 15° C. The freshly collected semen in each of the extender mediums was used to artificially inseminate turkey hens. One portion of each extender medium containing turkey semen was used immediately, that is, at zero storage time, to inseminate one group of turkey hens, and a second portion was stored at 15° C. for 6 hours before being used to inseminate a second group of turkey hens. The process was repeated each week using the same male turkeys and the same two groups of turkey hens for the 15 week period. For each insemination, 0.05 ml of extender-semen mixture was used. In view of the fact that, as noted above, researchers had stated that turkey spermatozoa retain full fertility in media having wide ranges in both osmolarity and pH level, the significantly improved performance of BPSE-II over that of BPSE-I is both surprising and unexpected.

In addition, I also found that freshly collected turkey semen containing live spermatozoa can be stored in vitro in BPSE-II without loss of fertility for 18 hours at 5° C. This discovery provides a convenient temperature and storage time range over which turkey semen can be stored without loss of fertility.

In the practice of this invention the extender medium is prepared as described above. Semen is collected from a plurality of male birds either directly into the medium or into a tube and the semen then mixed with the medium. The semen and medium are mixed at a 1:1 ratio on a volume basis. The mixture of semen containing live spermatozoa and medium can be stored in vitro for up to 6 hours at 15° C. or for up to 18 hours at 5° C. without loss of fertilizing capacity. The mixture of semen and extender medium is used to inseminate a plurality of female birds.

One of the important benefits provided by this invention is the reduction in manpower required to artificially inseminate a large number of female birds. Collected semen does not have to be used immediately; it can be collected and kept for up to 18 hours without loss of fertilizing capacity before being used.

As previously noted, in the process of artificially inseminating a plurality of female birds with a 1:1 mixture of semen and BPSE-II which had been stored at 15 C for 6 hours before being used, I unexpectedly found that the original levels of fertility, that is, the levels of fertility of the semen used immediately upon being collected and mixed at a 1:1 ratio in the extender medium (zero storage time) was maintained throughout the 24 week reproduction cycle of turkey hens. The same procedure was used in this 24 week reproduction cycle as that previously described with reference to the 15 week egg production period shown in Table 2.

Although 0.05 ml of extender semen mixture was used for each insemination in obtaining the results noted above, I have since found that this amount can be halved to 0.025 ml per insemination without any loss in effectiveness.

TABLE 1

| Primary Function | Constituent |
|---|---|
| Buffer | TES, Phosphates (Na or K), TRIS |
| Energy source | Fructose, Glucose, Inositol, Raffinose |
| Chelator | Glutamate, albumen, milk |
| Osmotic balance | Magnesium chloride and sodium acetate, Potassium citrate and sodium chloride |
| Antibacterial | Gentamycin, Penicillin Streptomycin |

TABLE 2

| | | | Weeks in Egg production | | | | | | |
|---|---|---|---|---|---|---|---|---|---|
| | | | 1-5 | | 6-10 | | 11-15 | | 1-15 |
| | | Storage | | | | | | | |
| Extender | pH | OP[1] | hr → 0 | 6 | 0 | 6 | 0 | 6 | 0 | 6 |
| | | | Fertility, % | | | | | | |
| BPSE-I | 7.5 | 333 | 94 | 92 | 93 | 82* | 95 | 63* | 94 | 79* |
| BPSE-II | 6.5 | 350 | 95 | 94 | 96 | 97 | 87 | 93 | 93 | 95 |

*Significantly P<.05) lower than 0 hr. treatment for the same production period.
[1]Osmotic pressure (osmolarity)

I claim:

1. A medium for preserving and extending the viable useful life of turkey semen, in vitro, comprising a mixture of salts, sugar and amino acids in amounts effective in aqueous solution to extend the viability of said semen, said mixture of salts, sugar and amino acids being chemically balanced to provide the proper osmotic balance, hydrogen ion concentration, chelating action and energy required to extend the viability of the semen and wherein the pH of the solution is about 6.5 and the osmolarity is about 350 m. osmols.

2. The medium of claim 1 in admixture with semen containing live spermatozoa.

3. A medium for extending the fertility of turkey semen for up to six hours when held in vitro at 15° C. and for up to 18 hours when held in vitro at 5° C., comprising a mixture of di-potassium phosphate, sodium glutamate, fructose, sodium acetate, mono-potassium phosphate, potassium citrate, magnesium chloride, and TES, said mixture having the proper pH and osmotic balance or osmolarity to extend the fertility of the semen, and wherein the pH of the solution is about 6.5 and the osmolarity is about 350 m. osmols.

4. The medium of claim 3 in admixture with semen containing live spermatozoa.

5. A medium for preserving and extending, in vitro, the useful life of turkey semen containing live spermatozoa and for maintaining high levels of fertility throughout a turkey hen reproduction cycle consisting of the formulation:

| Constituent | Grams |
| --- | --- |
| Potassium diphosphate . $3H_2O$ | 12.70 |
| Sodium glutamate | 8.67 |
| Fructose (anhydrous) | 5.00 |
| Sodium acetate . $3H_2O$ | 4.30 |
| TES* | 1.95 |
| Potassium citrate | 0.64 |
| Potassium monophosphate | 0.65 |
| Magnesium chloride . $6H_2O$ | 0.34 |

*N-tris Hydroxymethyl methyl-2-Aminoethane Sulfonic Acid.

said medium being formulated in aqueous solution and said medium having a pH of 6.5±0.1 and an osmolarity of 350±10 m. osmols.

6. A method for preserving turkey semen comprising mixing turkey semen containing live spermatozoa with an aqueous medium containing a mixture of salts, sugar and amino acids in amounts effective in aqueous solution to extend the visibility of said semen, said mixture of salts, sugar and amino acids being chemically balanced to provide the proper osmotic balance, hydrogen ion concentration, chelating action and energy required to extend the viability of the semen and wherein the pH of the solution is about 6.5 and the osmolarity is about 350 m. osmols.

7. The method of claim 6 wherein the semen is collected from a plurality of male birds directly into said aqueous medium in a container and the mixture of semen and medium after storage in said container is used to inseminate a plurality of female birds.

8. The method of claim 6 wherein the mixture of semen and medium is stored at 15° C.

9. The method of claim 6 wherein the mixture of semen and medium is stored at 5° C.

10. A method for preserving turkey semen containing live spermatozoa and for maintaining high levels of fertility throughout a turkey hen reproduction cycle, comprising mixing said turkey semen with an aqueous medium having the formulation:

| Constituent | Grams |
| --- | --- |
| Potassium diphosphate . $3H_2O$ | 12.70 |
| Sodium glutamate | 8.67 |
| Fructose (anhydrous) | 5.00 |
| Sodium acetate . $3H_2O$ | 4.30 |
| TES* | 1.95 |
| Potassium citrate | 0.64 |
| Potassium monophosphate | 0.65 |
| Magnesium chloride . $6H_2O$ | 0.34 |

*N-tris Hydroxymethyl methyl-2-Aminoethane Sulfonic Acid.

said medium having a pH of 6.5±0.1 and an osmolarity of 350±10 m. osmols.

11. A method for preparing a composition for extending the useful life of turkey semen comprising making a composition consisting of the formulation:

| Constituent | Grams |
| --- | --- |
| Potassium diphosphate . $3H_2O$ | 12.70 |
| Sodium glutamate | 8.67 |
| Fructose (anhydrous) | 5.00 |
| Sodium acetate . $3H_2O$ | 4.30 |
| TES* | 1.95 |
| Potassium citrate | 0.64 |
| Potassium monophosphate | 0.65 |
| Magnesium chloride . $6H_2O$ | 0.34 |

*N-tris Hydroxymethyl methyl-2-Aminoethane Sulfonic Acid.

said composition being formulated in aqueous solution and said aqueous solution being adjusted to a pH of 6.5±0.1 and an osmolarity of 350±10 m. osmols.

12. The method of claim 11 wherein the pH is adjusted by the addition of 12 N HCl and the osmolarity is adjusted by the addition of water.

* * * * *